United States Patent [19]

Yau

[11] Patent Number: 4,793,174

[45] Date of Patent: Dec. 27, 1988

[54] DIFFERENTIAL PRESSURE CAPILLARY VISCOMETER

[75] Inventor: Wallace W. Yau, Wilmington, Del.

[73] Assignee: E. I. Du Pont de Nemours and Company, Wilmington, Del.

[21] Appl. No.: 104,108

[22] Filed: Oct. 5, 1987

[51] Int. Cl.[4] .......................................... G01N 11/04
[52] U.S. Cl. ........................................................ 73/55
[58] Field of Search ........................ 73/54, 53, 61.1 C

[56] References Cited

U.S. PATENT DOCUMENTS

| | | | |
|---|---|---|---|
| 3,808,877 | 5/1974 | Blair | 73/55 |
| 4,165,632 | 8/1979 | Weber et al. | 73/55 |
| 4,384,472 | 5/1983 | Tournier | 73/55 |
| 4,478,071 | 10/1984 | Lecacheux et al. | 73/55 |
| 4,578,990 | 4/1986 | Abbott et al. | 73/55 |
| 4,627,271 | 12/1986 | Abbott et al. | 73/55 |

Primary Examiner—Stewart J. Levy
Assistant Examiner—Hezron E. Williams

[57] ABSTRACT

An improved differential pressure capillary viscometer in which a sample of solute in solution with a solvent is introduced into a stream of flowing solvent. The sample passes sequentially into first and second capillary tubes in which pressure differences are measured as a function of time. The pressure differences can be related to the viscosity of the sample.

11 Claims, 4 Drawing Sheets

DIFFERENTIAL PRESSURE CAPILLARY VISCOMETER

FIELD OF THE INVENTION

This invention relates to capillary viscometers, and more specifically, to differential pressure capillary viscometers which may be used to measure the viscosity of fluids, especially with chromatography apparatus to obtain accurate viscosity information for determining molecular weight distributions of multi-component samples.

BACKGROUND OF THE INVENTION

U.S. Pat. Nos. 4,578,990 and 4,627,271 describe a differential pressure capillary viscometer which may be used to measure viscosity independent of flow rate and temperature fluctuations. These patents disclose a viscometer in which a solvent is pumped from a reservoir into a system comprising a solute injection valve upstream of two capillary tubes which are separated by a large depository column which is used to trap solute, so that only solvent flows through the second capillary tube. Changes in pressure across both capillary tubes are measured and converted into electrical signals, which are fed to a differential logarithmic amplifier. The output signal of the differential logarithmic amplifier is related to the natural logarithm of the relative viscosity $\eta_r$. Both the inherent and intrinsic viscosities may be related mathematically to the experimentally measured value for the relative viscosity. Although the apparatus disclosed in these patents provides a viscosity measurement which is independent of flow rate and temperature fluctuations, there is a danger that after multiple uses the solute which has been retained by the large depository column, may begin to elute and affect the pressure changes in the second capillary tube, thereby leading to inaccuracies in the viscosity measurement.

Accordingly, there is a need in the art for a differential pressure capillary viscometer which is not only capable of measuring viscosity independent of flow rate and temperature fluctuation, but which is not subject to the potential for inaccuracy which is inherent in the prior art device discussed above.

SUMMARY OF THE INVENTION

This need is met by the present invention which, in one aspect, is a method for measuring either the inherent viscosity or intrinsic viscosity of a solute in solution with a solvent, comprising:

passing a stream of the solvent at a flow rate R through a first capillary tube and a second capillary tube which are separated from each other by an offset volume $\Delta V$, where $0 < \Delta V \leq RT$, where T is as defined below:

introducing into said stream of solvent, upstream of said first and second capillary tubes, a substantially localized volume of a solution comprising the solute and the solvent;

measuring, as a function of time, pressure differences $\Delta P_1(t)$ and $\Delta P_2(t)$ across said first and second capillary tubes, said $\Delta P_1(t)$ and $\Delta P_2(t)$ being characterized by a rise time T;

measuring, as a function of time, the concentration C(t) of the solute in the solvent; obtaining a function S(t), where $S(t) = \ln[\Delta P_1(t)/\Delta P_2(t)]$, where $S(t) = 0$ when solvent is flowing through both the first and second capillary tubes;

obtaining a function I(t), where $$I(t) = \int S(t) dt;$$

and relating C(t), I(t) and $\Delta V$ to the inherent or intrinsic viscosity of the solute in solution with the solvent.

In its second aspect, the invention is an apparatus specially adapted to carry out the above method.

DETAILED DESCRIPTION OF THE INVENTION

Figure 1:
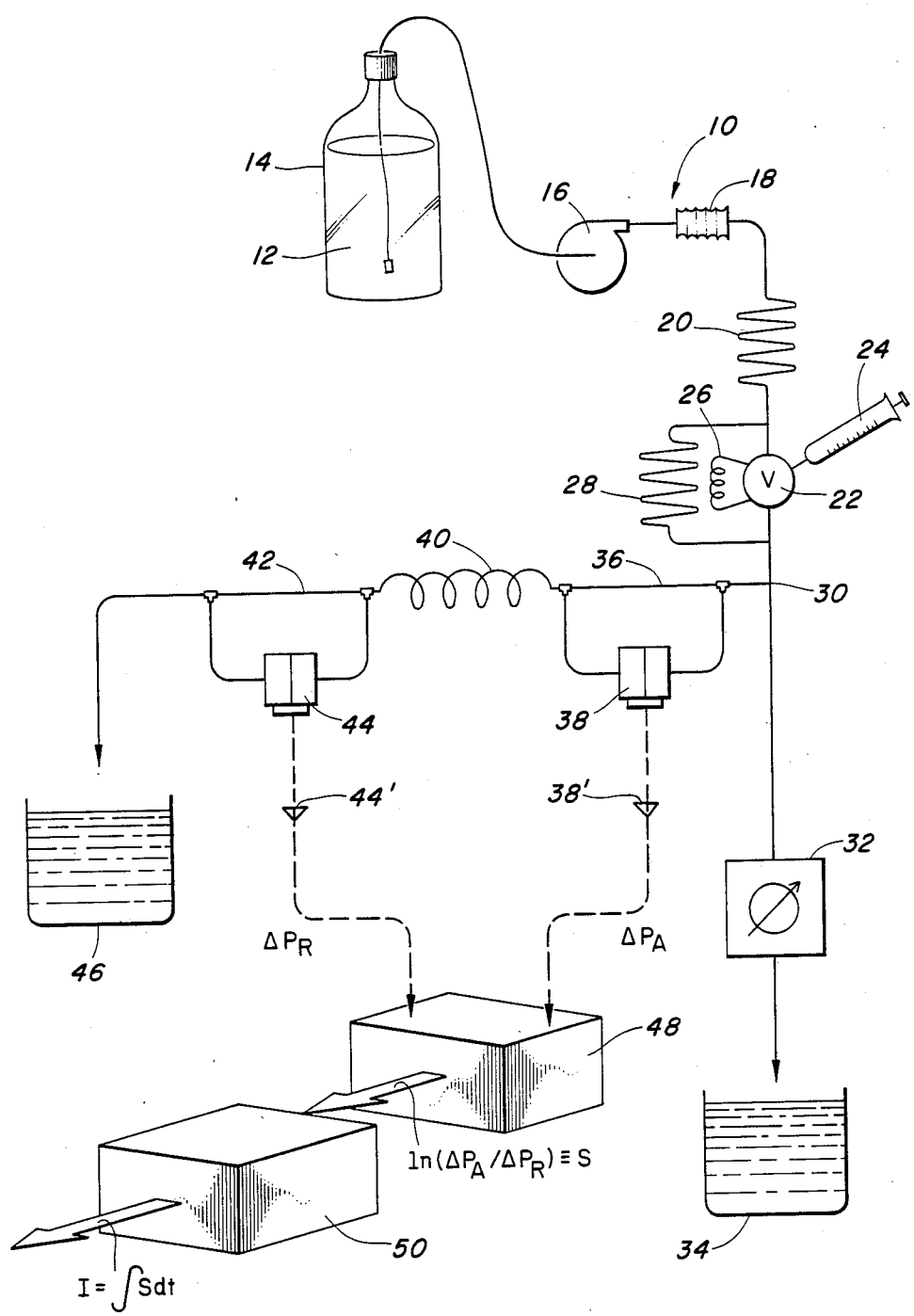
FIG. 1 is a schematic diagram of a stand-alone viscometer in accordance with the present invention.

Referring now to the figures, in which like reference numerals indicate like elements, there is seen in FIG. 1 an apparatus 10 in accordance with the present invention. A solvent 12 is pumped from a reservoir 14 by a pump 16 through a pulse dampener 18 and a flow resistor 20 to a sample injection valve 22. The pump 16 may be any type of pump which is used conventionally in liquid chromatography. Suitable pumps include piston-type pumps, as well as constant pressure pumps. The dampener 18 is required only if a reciprocal piston-type pump is used. Typically, the dampener will be chosen to dampen high frequency pulses without impeding the overall flow rate of the solvent 12. The tubing utilized in the apparatus is not critical. Generally, any small internal diameter tubing which is substantially chemically inert with respect to the solvent and solute may be utilized. Preferred tubings are made of stainless steel or Teflon ® (polytetrafluoroethylene), which is available from E. I. du Pont de Nemours & Company, Wilmington, Del.

The sample injection valve 22 may be a 2-position 6-port valve. A suitable valve is sold by Valco Instruments, Inc. (Houston, Tex.) under the designation CV6UHPA.

Conveniently, a syringe 24, containing solute in solvent ("sample solution"), may be utilized to fill sample loop 26 with sample solution. The sample injection valve 22 will be set to "load" position, which allows the solvent 12 to flow across the valve, while allowing sample loop 26 to be filled from syringe 24.

After sample loop 26 is filled with sample solution, valve 22 will be set to "inject" position, which diverts the flow of solvent 12 to sample loop 26. The sample solution will then be introduced into the flowing stream of solvent 12 as a substantially localized volume. A second flow resistor 28 may be placed across the sample valve to minimize flow disturbances.

The stream of flowing solvent 12, now containing a substantially localized volume of the sample solution (comprising the solute and the solvent), can be split at a junction 30, so that a portion of the stream passes through a concentration detector 32 into a waste receptacle 34 and another portion passes to first and second capillary tubes, discussed below. Alternatively, the concentration detector 32 can be placed in series with the capillary tubes 36 and 42, discussed below. The concentration detector 32 may be any type of detector which is typically used in liquid chromatography. A preferred concentration detector 32 is a differential refractometer. Other types of concentration detectors such as ultraviolet or infrared devices also may be used, depending upon the particular type of solute whose viscosity is being measured.

The flowing solvent stream—containing the substantially localized volume of sample solution—will pass through a first capillary tube 36, across which differences in pressure as a function of time will be detected by transducer 38. The sample will continue to flow through an offset volume element 40 into a second capillary tube 42, across which differences in pressure as a function of time will be detected by transducer 44. Finally, the solution will be emptied into a waste receptacle 46.

The internal diameter of the capillary tubes 36, 42 is not critical. Generally, the internal diameter will be chosen to maximize the performance of the pressure transducers associated with each capillary tube. Generally, the internal diameter will be larger than 7 mil. It is preferred that capillary tubes 36 and 42 be as close to physically identical as possible.

The pressure transducers can be the well-known diaphragm type such as those manufactured by Celesco Transducer Products, Inc. (Conoga Park, Calif.). Typically, the transducers 38, 44 are connected across their respective capillary tubes 36, 42 by means of "T" connectors. Each pressure transducer 38, 44 is connected to its own amplification means 38', 44', respectively, with variable gain control. Preferably the amplification means comprises a DC amplifier. The variable gain controls are used to control the magnitude of the outputs from the two pressure transducers. Specifically, the two gains will be adjusted to provide equal outputs when the same solution, e.g. the solvent, is flowing through capillary tubes 36 and 42. It will be appreciated that under these conditions the function S(t) will equal zero.

Advantageously, the fluid circuit defined by the apparatus 10 will be placed in a bath (not shown) at a preselected temperature. The bath will help to minimize temperature gradients within the apparatus.

It will be appreciated that unlike the device described in U.S. Pat. No. 4,578,990 and 4,627,271, in which solvent alone flows through one capillary and sample solution flows through the other, in the present invention the solvent stream containing the substantially localized volume of sample solution flows through both capillary tubes.

The outputs from transducers 38 and 44 can be applied to the inputs (not shown) of a differential logarithmic amplifier 48. A suitable amplifier is a Burr Brown Log 100 JP. The output signal of the differential logarithmic amplifier 48 can be expressed by the following equation: $S(t)=\ln[\Delta P_1(t)/\Delta P_2(t)]$. This output is a function of time. The output S(t) is then integrated over time. The integration can be manual, electronic, or computerized. If the integration is manual, the area under the S(t) curve will be determined by well-known computational methods. Advantageously, the output of the differential logarithmic amplifier is applied to the input (not shown) of an electronic integrator or digital computer, indicated generally by the reference numeral 50. A suitable electronic integrator is a Hewlett Packard 3392A (Sunnyvale, Calif.).

The apparatus in accordance with the present invention allows a stream of solvent containing a substantially localized volume of solution, to pass sequentially through two capillary tubes separated by a small offset volume. As the substantially localized volume of solution passes through each capillary tube, the pressure difference across the tube will rise from a baseline to a maximum value in a characteristic rise time (T). As the substantially localized volume of solution leaves each capillary tube, the pressure difference across the tube will decay back to baseline in a characteristic decay time, which should approximate the rise time. After the substantially localized volume of solution has passed through both capillary tubes, the respective pressure transducers will have generated two substantially identical pressure versus time curves, which curves are separated from one another by a time difference, $\Delta T$, which is equal to the offset volume $\Delta V$ divided by the flow rate R. When $\Delta T$ is sufficiently small, the two pressure versus time curves will be slightly displaced from one another, thereby allowing one curve to be used to approximate a value on the other curve. Generally, this condition will be achieved when the offset volume $\Delta V$ lies between 0 and RT.

The viscometer according to the present invention is based upon the following mathematics.

A small time difference between the $\Delta P$ responses of the two pressure transducers can be related to a volume difference $\Delta V$, which is equal to the volume offset. In addition, time, t, can be related to volume passing through the apparatus by the equation $v = Rt$ where R is the flow rate. The responses $\Delta P_1(t)$ and $\Delta P_2(t)$ are, therefore, also functions of volume, i.e., $\Delta P_1(v)$ and $\Delta P_2(v)$.

If one defines $Y_1(v) = \ln[\Delta P_1(v)]$ and $Y_2(v) = \ln[\Delta P_2(v)]$, then one can define a function S(v) where $S(v) = Y_1(v) - Y_2(v)$.

But for a small $\Delta v$, $Y_1(v)$ can be related to $Y_2(v)$ by the approximation $Y_1(v) \cong Y_2(v+\Delta v)$. This approximation will hold when the capillaries are physically identical. Because capillaries are not physically identical in fact, the pressure transducers 38 and 44 can be connected to amplification means having adjustable electronic gains, which will be adjusted to provide identical outputs in response to the pressure differences resulting from the same calibration solution, e.g., the solvent.

A Taylor series expansion of $Y_2(v)$ about a point v gives $Y_2(v+\Delta v) \approx Y_2(v) + Y_2'(v)\Delta v + Y_2''(v)(v^2/2) + \ldots$ where $Y_2'(v)$ and $Y_2''(v)$ are the first and second derivatives of $Y_2(v)$ with respect to volume. If $\Delta v$ is small, the series can be truncated after the first derivative, i.e., $$Y_2(v+\Delta v) \approx Y_2(v) + Y_2'(v)\Delta v.$$

Substituting the series into the equation for S(v), one gets $$S(v) = Y_2'(v)\Delta v.$$

Integrating with respect to volume, one gets a new function I(v) where $$I(v) = \int_{v_1}^{v_2} S(v)dv = \int_{v_1}^{v_2} Y_2'(v)\Delta v dv$$

$$= Y_2(v)\Delta v \Big|_{v_1}^{v_2}$$

If $v_1$ is a volume when the pressure transducers are sensing pure solvent, and $v_2$ is a volume where the transducers are sensing solution, $$I(v) = \Delta v[Y_2(v)_{sol'n} - Y_2(v)_{solvent}]$$

or $$\frac{I(v)}{\Delta v} = [\ln \Delta P_2(v)_{sol'n} - \ln \Delta P_2(v)_{solvent}]$$

$$= \ln \left[\frac{\Delta P_2(v)_{sol'n}}{\Delta P_2(v)_{solvent}}\right]$$

The value $\Delta P$ can be related to viscosity, generally, by the formula $$\Delta P = GKR\eta,$$

where
 G is the electronic gain;
 K is a constant, dependent upon the geometry of the capillary;
 R is the flow rate; and
 $\eta$ is viscosity.
Hence, $$\frac{I(v)}{\Delta v} = \left[\ln \frac{GKR\eta_{sol'n}}{GKR\eta_{solvent}}\right]$$

$$= \left[\ln \frac{\eta_{sol'n}}{\eta_{solvent}}\right]$$

$$= \ln \eta_r$$

where $\eta_r$, the relative viscosity, is the ratio of $\eta_{sol'n}$ to $\eta_{solvent}$.

The inherent and intrinsic viscosities, $\eta_{inh}$ and $[\eta]$, can be related to $\eta_r$ as follows:

$$\eta_{inh} = (ln\eta_r/C)$$

where C is concentration, and $$[\eta] = \lim_{C \to 0} \frac{\ln \eta_r}{C}$$

$$\eta_{inh} = \frac{I(v)}{\Delta v C(v)}, \text{ and}$$

$$[\eta] = \lim_{C \to 0} \eta_{inh}.$$

The foregoing approximation can be used to advantage when at least a portion of the substantially localized volume of solution simultaneously occupies both capillaries for at least some period of time. This condition can be achieved if the offset volume, $\Delta V$, is chosen such that $0 < \Delta V \leq RT$, where
 R = flowrate
 T = rise time.

The offset volume $\Delta V$ can then be substituted for $\Delta v$ in the foregoing equations.

The rise time is defined as that time during which the pressure differences as measured by either of the pressure transducers 38 or 44, rises from baseline to maximum. (The decay time should closely approximate rise time, and may also be used.)

Figure 2:
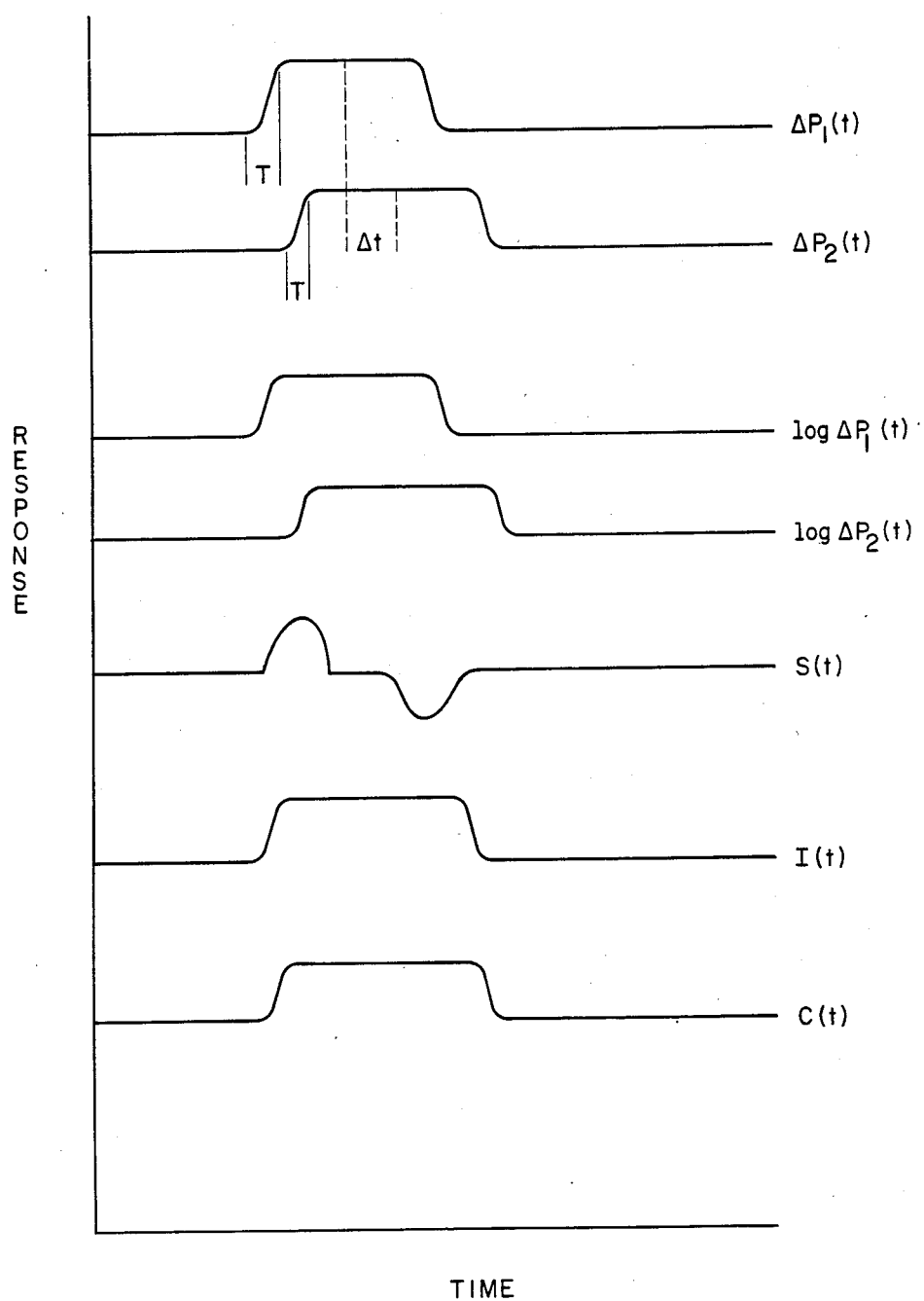
FIG. 2 is a graph illustrating stylized signal outputs of the concentration detector, the differential logarithmic amplifier, and the integrator of the apparatus of FIG. 1.

A typical rise time T is shown in FIG. 2, which also shows a typical output of the pressure transducers 38 and 44, differential logarithmic amplifier 48, integrator 50 and concentration detector 32.

The log of the relative viscosity, $\eta_r$, can be obtained by dividing any point on the plateau of the I(t) curve by the offset volume $\Delta V$. The inherent viscosity, $\eta_{inh}$, can be obtained by dividing ln $\eta_r$ by the value of C(t) obtained at a point on the plateau of the C(t) curve.

The offset volume $\Delta V$ may be obtained by direct physical measurement of the volume of the offset volume element 40, or it may be obtained experimentally. The experimental route is preferred because it is generally more accurate than physical measurement. To obtain an experimental value for $\Delta V$, a solution containing a solute of known viscosity can be injected into the apparatus 10. A resulting C(t) curve and I(t) curve will be obtained. Dividing any point on the plateau of the I(t) curve by a corresponding point on the C(t) curve will equal the product of $\Delta V$ times $\eta_{inh}$. $\Delta V$ may be obtained by dividing the I(t)/C(t) ratio by the known viscosity value, $\eta_{inh}$. This calculation, in effect, provides a calibration value for $\Delta V$ which can be used in all subsequent measurements using the apparatus 10.

Figure 3:
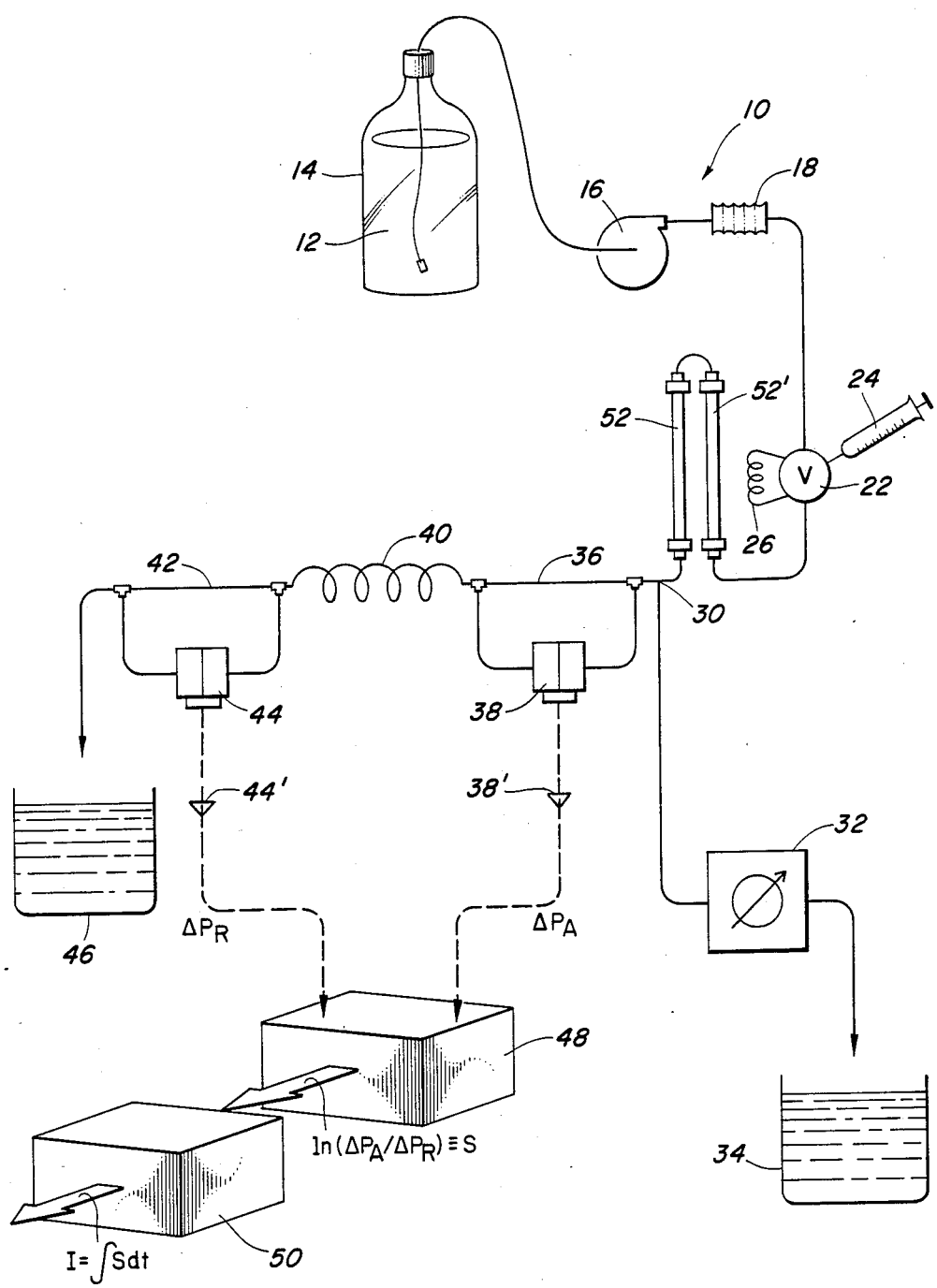
FIG. 3 is a schematic diagram of the viscometer of the present invention together with gel permeation chromotography apparatus.

FIG. 3 is a schematic representation of a gel permeation chromotography (GPC) (also referred to as size exclusion chromatography) viscometer in accordance with the present invention. The apparatus 10 is substantially equivalent to that shown in FIG. 1. Flow resistors 20 and 28 have been eliminated. Intermediate the sample injection valve 22 and the junction 30 is a GPC column 52 which may be used in series with other columns, shown diagramatically as 52'.

The substantially localized volume of sample solution, after having been injected into the stream of flowing solvent, will enter GPC column 52 where components in the sample solution will be separated according to their molecular weight. A substantially localized volume for each component in the sample will elute from the column 52. A portion of each such localized volume will pass through the concentration detector 32 (which, as explained above, also may be in series with the capillary tubes 36, 42) and sequentially through the first capillary tube 36, offset volume 40, and second capillary tube 42. Accordingly, each such component will produce a separate concentration peak, as well as a $\Delta P_1(t)$ and $\Delta P_2(t)$.

Figure 4:
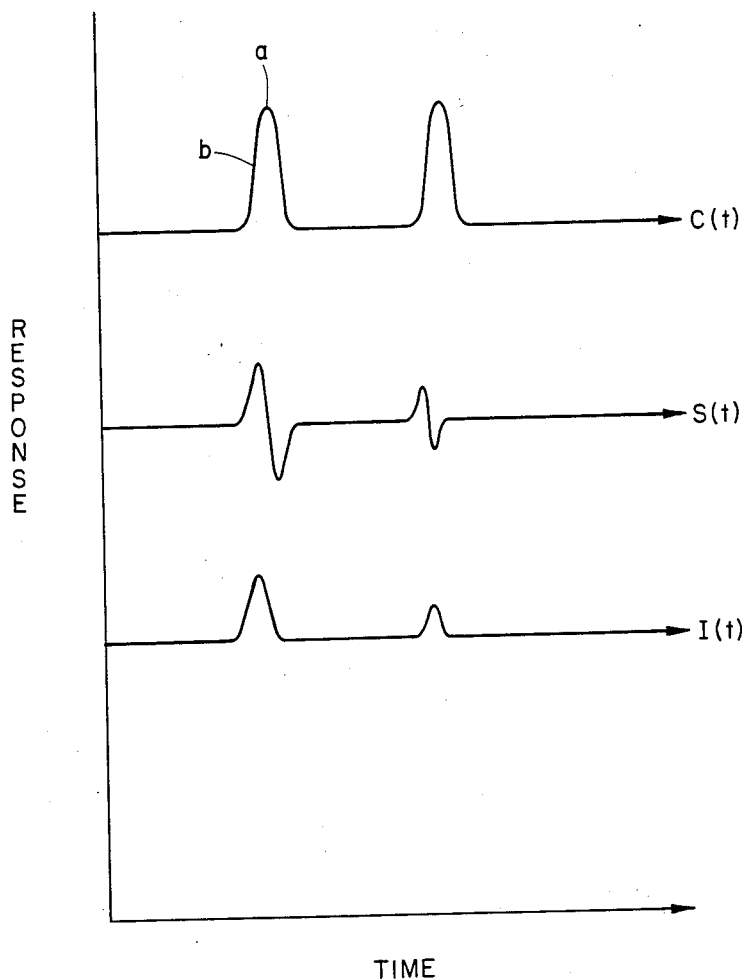
FIG. 4 is a graph illustrating stylized signal outputs of the concentration detector, the differential logarithmic amplifier, and the integrator of the apparatus in FIG. 3.

FIG. 4 depicts stylized outputs obtained from a 2-component system applied to the apparatus of FIG. 3. FIG. 4 shows the output C(t) of the concentration detector 32. The figure also shows the function S(t) and the function I(t). From the figure, it can be seen that a sample solution containing equal concentrations of two different molecular weight components passed through the apparatus 10. It will be appreciated that although the concentrations of the two components are equal (as can be seen from the equal heights of the two peaks in the C(t) curve), the two peaks of the I(t) curve are not equal due to the different viscosities.

The viscosities of the two components can be calculated manually from the curve, or may be obtained by using electronic equipment or a digital computer.

If manual means are employed, the outputs of the pressure transducers 38 and 44 may be applied to the inputs of a strip chart recorder, which is capable of providing a trace as a function of time. From such traces, a third curve representing S(t) may be obtained. The area under the S(t) curve may be plotted as a function of time to obtain an I(t) curve. Any point on the I(t) curve may be divided by the corresponding point on C(t) curve to obtain the inherent viscosity times the offset volume. As in the stand-alone viscometer shown in FIG. 1, the offset volume may be measured by directly measuring the volume of offset volume element 40, or may be determined experimentally by passing through the apparatus 10 a calibration solution containing a solute of known viscosity.

It is preferred to take the peak values, designated by "a" on the C(t) and I(t) curves to calculate inherent viscosity. Use of the peak values, rather than shoulder values, designated "b", generally results in a more accurate result because of the better signal to noise ratio at the peak value, "a".

If each peak itself represents a multi-component phase, the area under each I(t) peak can be divided by the area under the corresponding C(t) peak to obtain an average inherent viscosity times $\Delta V$.

Although the inherent viscosity may be calculated, as described above, it is preferred to obtain the result by electronic means. Advantageously, the outputs of the pressure transducers 38 and 44 may be applied directly to the inputs (not shown) of the differential logarithmic amplifier 48. The output of the amplifier 48 may be applied to the input (not shown) of an integrator 50, which may be an electronic integrator or a digital computer.

Although the apparatus 10, as described above, comprises a separate first and second capillary tube separated by a discrete offset volume element, it will occur to those skilled in the art, that a single capillary tube may be utilized, provided a first pressure difference $\Delta P_1(t)$ is measured across only a portion of the tube, while the second pressure difference $\Delta P_2(t)$ is measured across the entire capillary tube. In this configuration, the offset volume, $\Delta V$, will be equal to the difference between half the volume of the entire capillary and half the volume of that portion of the capillary over which $\Delta P_1(t)$ is measured. Although such configuration is within the scope of the present invention, the use of two separate capillary tubes is preferred.

The method and apparatus of the present invention may be utilized to obtain relative viscosity measurements, as well as inherent and intrinsic viscosity measurements for a wide variety of solutes in solution. The principal utility of the invention resides in the measurement of such values for polymers.

Although specific embodiments of the present invention have been described, it will be apparent to those skilled in the art that departures and modifications may be made without departing from the present invention, which is defined by the claims which follow.

What is claimed:

1. A method for measuring either the inherent viscosity $\eta_{inh}$, or intrinsic viscosity, $[\eta]$, of a solute in solution with a solvent, comprising:

passing a stream of the solvent at a flow rate R through a first capillary tube and a second capillary tube which are separated from each other by an offset volume $\Delta V$, where $0 < \Delta V \leq RT$, where T is as defined below;

introducing into said stream of solvent, upstream of said first and second capillary tubes, a substantially localized volume of a solution comprising the solute and the solvent;

measuring, as a function of time, pressure differences $\Delta P_1(t)$ and $\Delta P_2(t)$ across said first and second capillary tubes, respectively, said $\Delta P_1(t)$ and $\Delta P_2(t)$ being characterized by a rise time T;

measuring, as a function of time, the concentration C(t) of the solute in the solvent;

obtaining a function S(t), where $$S(t) = ln[\Delta P_1(t)/\Delta P_2(t)],$$

and where S(t)=0 when solvent is flowing through both the first and second capillary tubes;

obtaining a function I(t), where $$I(t) = \int S(t)dt;$$

and relating C(t), I(t) and $\Delta V$ to the inherent or intrinsic viscosity of the solute in solution with the solvent.

2. The method of claim 1 wherein the function S(t) is obtained by the use of a differential logarithmic amplifier.

3. The method of claim 2 wherein the function I(t) is obtained by the use of an electronic integrator or a digital computer.

4. The method of claim 3 wherein the function C(t) is obtained by the use of a differential refractometer.

5. The method of claim 4 wherein the solution comprising the solute and the solvent is introduced into the stream of solvent through a valve which provides a solvent flow by-pass around the valve to provide continuous solvent flow during switching of the valve.

6. An apparatus for measuring either the intrinsic or inherent viscosity of a sample comprising a solute in solution with a solvent, comprising in combination:

a first capillary tube through which a stream of solvent-containing a substantially localized volume of the sample flows;

a second capillary tube arranged in series with the first capillary tube and through which a stream of solvent containing a substantially localized volume of the sample flows;

solvent supply means for supplying the solvent to flow through both capillary tubes; sample supply means for introducing the sample into the stream of solvent;

means for measuring pressure differences $\Delta P_1(t)$ and $\Delta P_2(t)$ as a function of time across the first and second capillary tubes, respectively, and generating signals corresponding to the pressure differences; and means for measuring the concentration of the solute as a function of time.

7. The apparatus of claim 6, further comprising amplification means for controlling the magnitude of the signals corresponding to the pressure differences, $\Delta P_1(t)$ and $\Delta P_2(t)$.

8. The apparatus of claim 7 wherein the means for measuring the concentration of the solute as a function of time comprises a differential refractometer.

9. The apparatus of claim 8 further comprising a differential logarithmic amplifier capable of providing an output S(t) as a function of time, where $$S(t)=ln[\Delta P_1(t)/\Delta P_2(t)].$$

10. The apparatus of claim 9 further comprising an electronic integrator or digital computer capable of providing an output I(t), where $$I(t)=\int S(t)dt.$$

11. The apparatus of claim 10 further comprising a gel permeation chromotography column intermediate the sample supply means and the first capillary tube.

* * * * *